United States Patent [19]
Krauss et al.

[11] Patent Number: 5,083,550
[45] Date of Patent: Jan. 28, 1992

[54] DEVICE FOR LOCATING AND DISINTEGRATING CONCRETIONS IN BODILY CAVITIES

[75] Inventors: Werner Krauss, Maulbronn; Helmut Wurster, Oberderdingen, both of Fed. Rep. of Germany

[73] Assignee: Richard Wolf GmbH, Knittlingen, Fed. Rep. of Germany

[21] Appl. No.: 369,318

[22] Filed: Jun. 20, 1989

Related U.S. Application Data

[62] Division of Ser. No. 888,715, Jul. 24, 1986, Pat. No. 4,869,239.

Foreign Application Priority Data

Sep. 12, 1985 [DE] Fed. Rep. of Germany ....... 3532678

[51] Int. Cl.$^5$ ............................................. A61B 17/22
[52] U.S. Cl. ............................ 128/24 EL; 128/653.1
[58] Field of Search ............... 128/24 A, 660.03, 653, 128/24 EL; 606/128

[56] References Cited

U.S. PATENT DOCUMENTS

| | | |
|---|---|---|
| 2,559,227 | 7/1951 | Rieber . |
| 3,990,296 | 11/1976 | Erikson . |
| 4,043,181 | 8/1977 | Nigam . |
| 4,094,306 | 6/1978 | Kossoff . |
| 4,298,009 | 11/1981 | Mezrich et al. . |
| 4,347,850 | 9/1982 | Kelly-Fry et al. . |
| 4,418,698 | 12/1983 | Dory . |
| 4,484,569 | 11/1984 | Driller et al. . |
| 4,539,989 | 9/1985 | Forssmann et al. . |
| 4,610,249 | 9/1986 | Makofski et al. . |
| 4,620,545 | 11/1986 | Shene et al. . |
| 4,630,607 | 12/1986 | Duinker et al. . |
| 4,669,483 | 6/1987 | Hepp et al. . |
| 4,705,026 | 11/1987 | Chaussy et al. . |
| 4,877,017 | 10/1989 | Hahn et al. ........................ 128/24 A |

FOREIGN PATENT DOCUMENTS

| | | |
|---|---|---|
| 0131654 | 1/1985 | European Pat. Off. . |
| 3220751 | 12/1983 | Fed. Rep. of Germany . |
| 2913251 | 8/1985 | Fed. Rep. of Germany . |
| 2140693 | 12/1984 | United Kingdom . |

OTHER PUBLICATIONS

F. J. Fry, "Intense Focused Ultrasound: Its Production, Effects and Utilization", Ultrasound: Its Applications in Medicine and Biology, vol. 3, Francis J. Fry, ed., Elsevier Scientific Publishing Co., 1978, pp. 689-736.

*Primary Examiner*—Ruth S. Smith
*Attorney, Agent, or Firm*—Panitch Schwarze Jacobs & Nadel

[57] ABSTRACT

A device for locating and disintegrating concretions and stones in bodily cavities by means of a shock wave generator comprises a reclining surface for the patient, with an opening therein below which the generator, including a flexible precursor section, is so arranged that the fluid sealed off from the outside is in contact via the opening with the body section to be treated, either directly or indirectly via a diaphragm sealing off the precursor section. To this end, the reclining surface and the shock wave generator are displaceable with respect to each other.

13 Claims, 5 Drawing Sheets

DEVICE FOR LOCATING AND DISINTEGRATING CONCRETIONS IN BODILY CAVITIES

This is a division of application Ser. No. 06/888,715, filed July 24, 1986, now U.S. Pat. No. 4,869,239.

BACKGROUND OF THE INVENTION

The invention relates to a device for locating and disintegrating concretions and stones in bodily cavities by means of a shock wave generator, from which shock waves are transmitted to the stone enclosed in the body via a coupling fluid in a flexibly constructed precursor fluid section, said fluid being in direct contact with the patient's body.

DESCRIPTION OF THE PRIOR ART

European patent 0084093 discloses a reclining support carrying a patient which may be dipped into a tub or bath filled with coupling fluid. A shock wave generator is then focussed on the concretion or stone which is to be disintegrated.

German patent specification 3220751 discloses a shock wave generator comprising a flexible precursor fluid section and a delimiting foil, for disintegrating stones. With this device, the need for a tub to be filled with a great quantity of fluid is averted, but the flexible precursor section has to be applied to the body manually with the foil and a coupling gel, and held in a particular position.

SUMMARY OF THE INVENTION

It is an object of the invention to provide a device which may be operated easily and conveniently for disintegrating concretions or stones by means of a shock wave generator. It is a further object of the invention to make it possible to move the patient to the setting required for locating and disintegrating a stone, as well as for X-ray verifications, without altering his position relative to the patient support.

The first said object is achieved in accordance with the invention in that a reclining surface for the patient is provided with an opening below which a shock wave generator is installed. This shock wave generator comprises a flexible precursor fluid section so installed that its fluid is sealed off in the outward direction. This fluid is placed in direct contact via the opening with the area of the patient's body which penetrates into the opening and is to be exposed to sonic action. Alternately, the fluid in the fluid section may be placed in indirect contact with the same via a precursor section divided into two chambers by means of a diaphragm.

The second said object is achieved in that the patient on the reclining surface may be moved omnilaterally with respect to the stationary shock wave generator (or conversely that the shock wave generator may be moved omnilaterally with respect to the stationary reclining surface) without to this end having to alter the patient's position on the reclining surface. In this way it is possible to obtain any setting required both for locating and disintegrating a stone and for X-ray verification.

By means of the invention, the flexible precursor fluid section of the shock wave generator (which may be of a type known per se) may be connected in a sealed manner to the reclining surface in direct contiguity to the opening and the upper opening rim may have arranged around it a coupling sealing ring which moulds itself in a sealed manner to the body, the area of the body which is to be exposed to sonic action penetrating into the opening, so that it is in direct contact with the fluid in a particularly advantageous manner, or is placed in close-fitting contact with a diaphragm which delimits the precursor section.

Furthermore, the flexible precursor fluid section of the shock wave generator may be connected directly to the patient on the reclining support, the upper edge of the flexible casing of the precursor section being hermetically joined to a bag which extends through the opening and is fastened to the body, advantageously by a belt. In this case too, the area of the body which is to be exposed to sonic action is placed in contact with the fluid of the shock wave generator indirectly via an elastic diaphragm.

Further objects and advantages of the invention will become apparent from the following description, taken in conjunction with the accompanying drawings wherein are illustrated preferred embodiments of the device according to the invention.

DETAILED DESCRIPTION OF THE PREFERRED EMBODIMENTS

Figure 1:
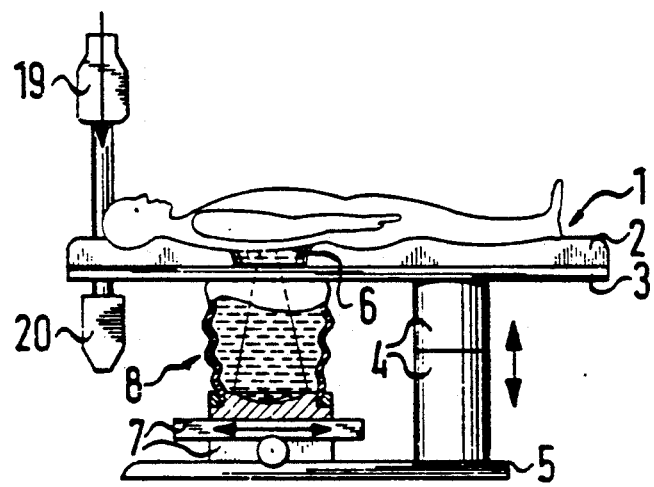
FIGS. 1 and 2 show two sideviews of a device for locating and disintegrating stones within the body of a patient and for X-ray verification thereof, as well as the shock wave generator, in axial cross-section, in alternative positions.

The device for locating and disintegrating concretions in bodily cavities comprises a reclining surface 1 formed by a support 2 for the patient and a reclining table 3, e.g. an operating table, the support 2 being displaceable in two dimensions on the table 3. This reclining surface 1 is supported by a pillar 4 mounted on a base 5 and is provided with an opening 6 on which the body section scheduled for sonic treatment is to be positioned and through which the body section engaged therein is exposed to the sonic action of shock waves to disintegrate a stone therein, by means of a shock wave generator 8, which may be moved and pivotally displaced tridimensionally on a displacing unit 7, and is utilizable in a known manner for locating and disintegrating a stone situated at its focus.

Figure 6:
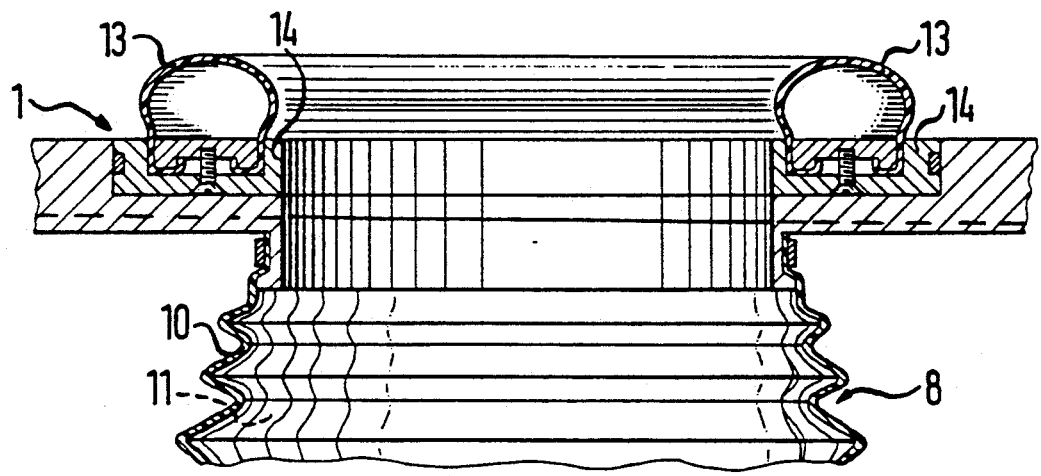
FIGS. 6 and 7 show two enlarged partial cross-sections through the reclining surface, with sealing of the precursor fluid section of the shock wave generator on the patient.
Figure 7:
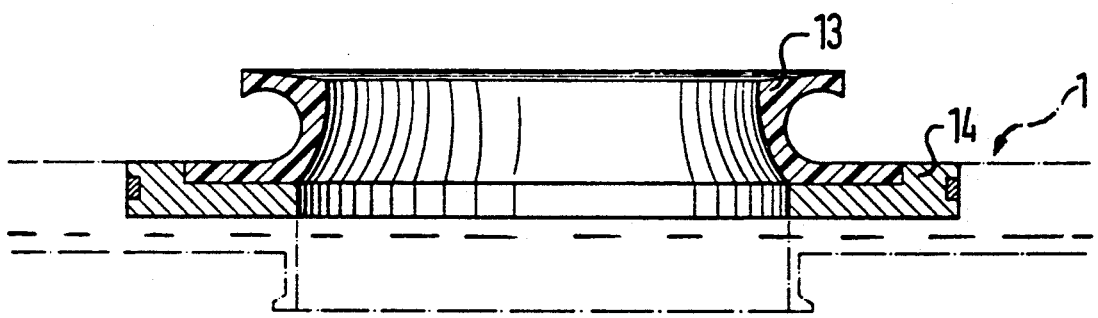

The source 9 of shock waves is surrounded by a flexible casing 10, which is fastened to the reclining surface 1 with the upper extremity sealed around the opening 6, and which is filled with a coupling fluid 11 as a precursor section. The body section scheduled to undergo sonic treatment dips into this fluid via the opening 6, the body section resting on an elastic ring 12 on the reclining surface 1, which seals off the precursor fluid section 11. The seal may also have the form of an annular hose 13 filled with water or gas as shown in FIG. 6 or of an elastic ring 13 as shown in FIG. 7, these seals 13 being exchangeably insertable in the reclining surface 1 by means of a fitting ring 14, depending on the size of the patient.

After the body section to be treated is placed in the area of the opening, the shock wave generator for disintegrating the stone has its focus adjusted on to the stone for location of the same, which is performed by omnilateral displacement of the shock wave generator 8 or of the reclining surface 1. The sonic treatment is particularly advantageous in the case of the embodiment according to FIGS. 1 to 3, since the fluid of the precursor section 11 is then in perfect direct contact with the body section to be treated. It is also possible however for the precursor section 11 to be delimited by a diaphragm or foil (as shown in phantom in FIG. 3) which moulds itself directly to the body or with the interpositioning of an appropriate gel.

Figure 2:
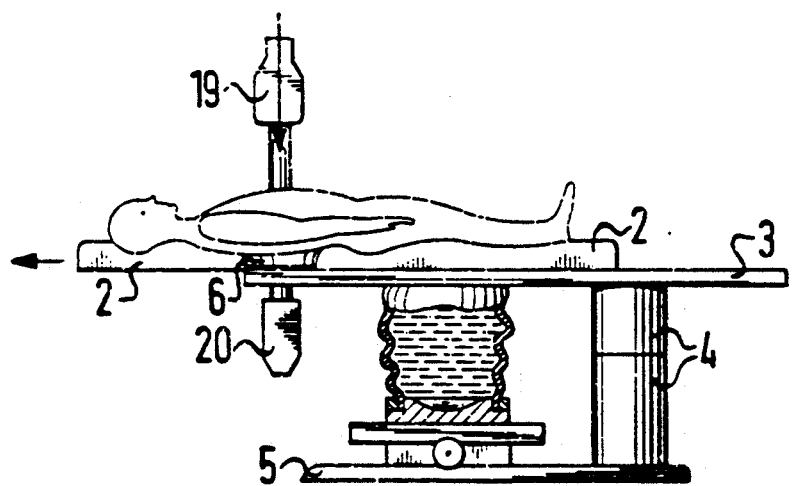
Figure 3:
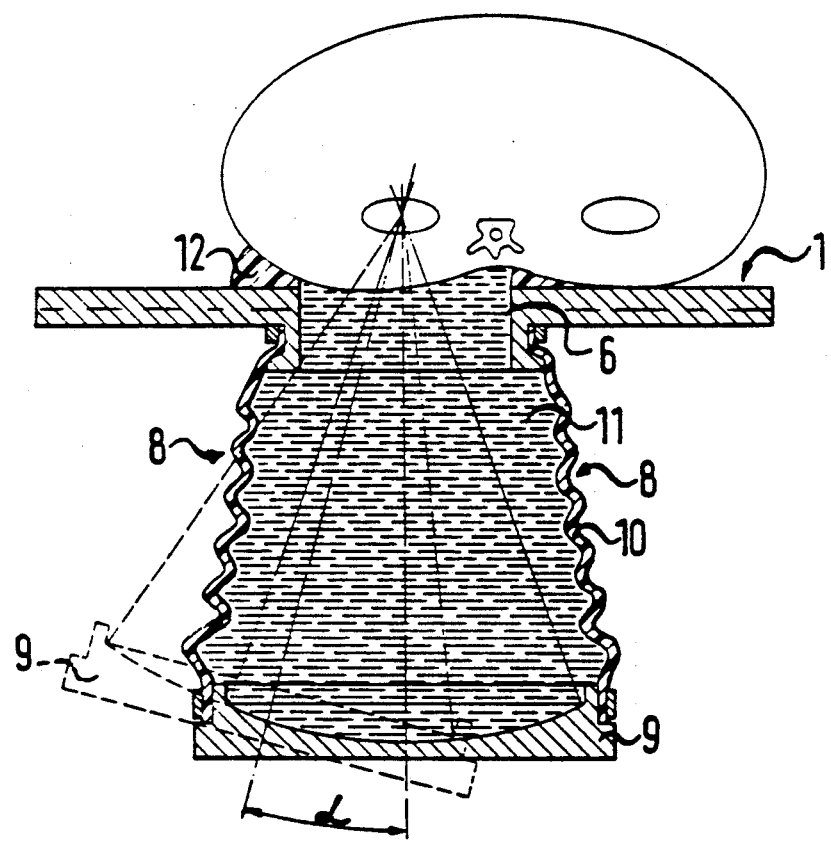
FIG. 3 shows an enlarged axial cross-section through the shock wave generator in conjunction with a reclining surface that supports the patient.
Figure 4:
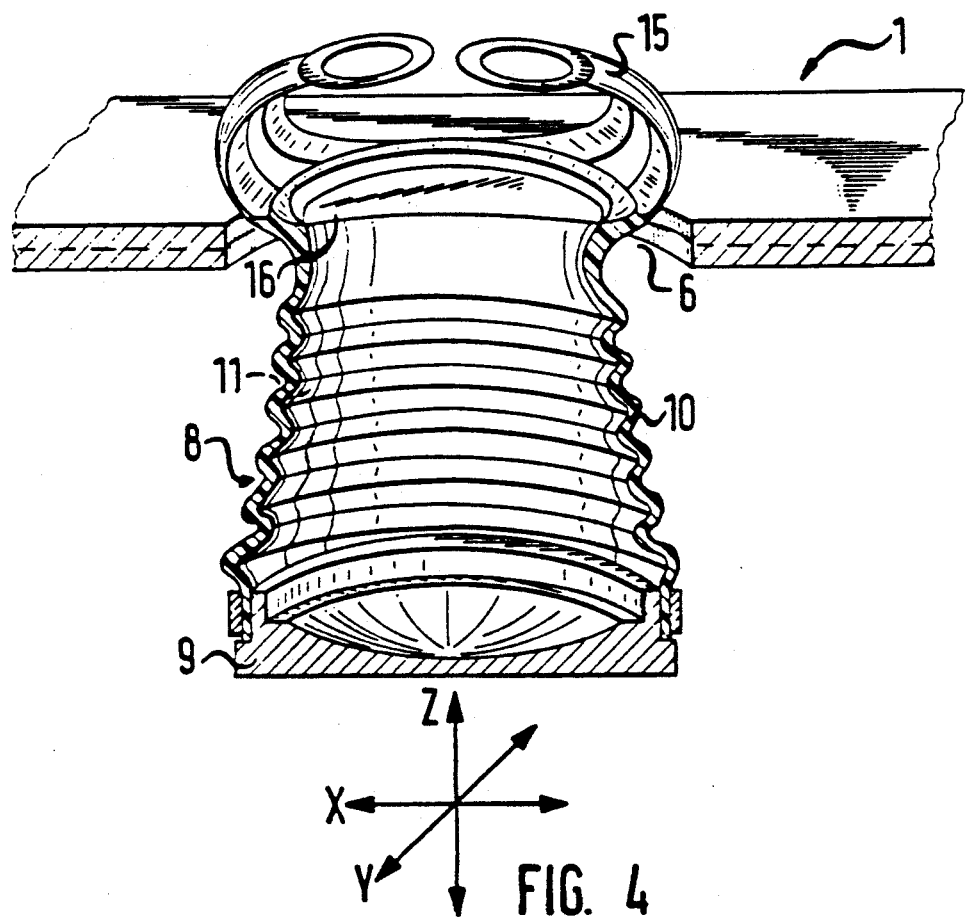
FIG. 4 shows a cross-section of a part of a reclining surface and of a shock wave generator connected directly to the patient.

Instead of the embodiment according to FIGS. 1 to 3, it is also possible to adopt the arrangement shown in FIG. 4, in which the upper edge of the flexible casing 10 of the shock wave generator is joined at its periphery to a belt 15 encircling the patient's body resting on the reclining surface 1, into a unit which projects freely through the opening 6 of the reclining surface 1. In this case, the fluid of the precursor section 11 will be in direct contact with the body section to be treated, or the precusor section 11 is closed off by a thin foil 16, so that a separate space is then formed between the foil 16, the body and the belt 15, which is filled with a fluid coming into contact with the body and forming a complement to the precursor section 11. The adjustment of the focus of the shock wave generator 8 is then performed again by omnilateral adjustment of the shock waves source 9 or of the reclining surface 1 together with the patient, relative to the stationary shock wave generator 8.

Figure 5:
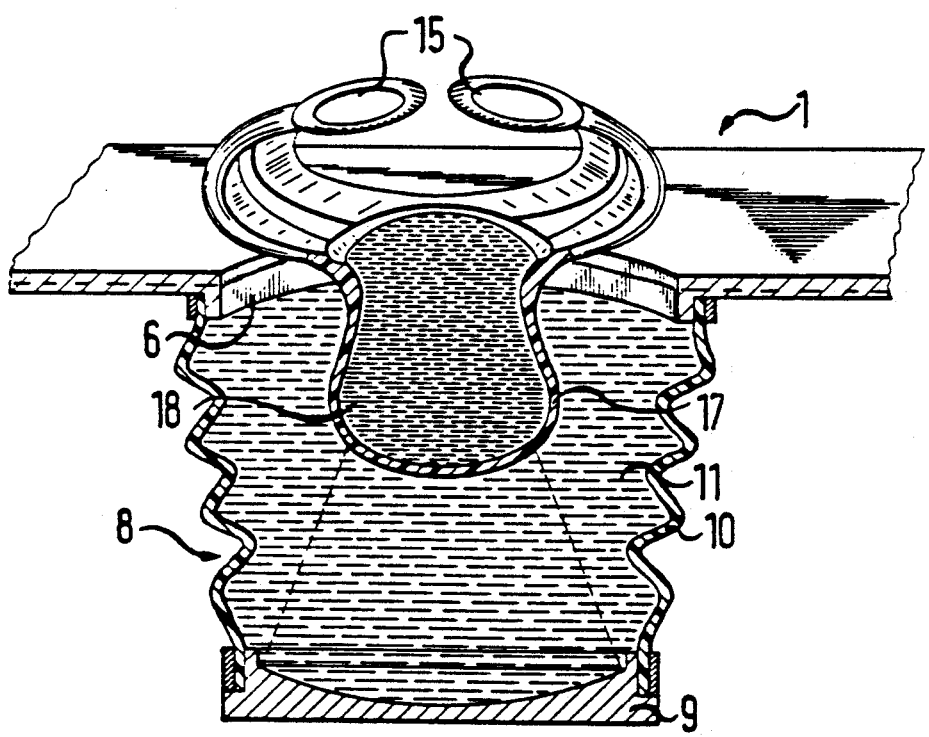
FIG. 5 shows an embodiment similar to that of FIG. 4, but with a modified method of coupling the shock wave generator to the patient's body.

According to FIG. 5, it is also possible for the casing 10 of the precursor fluid section 11 of the shock wave generator 8 to be joined in sealed manner to the reclining surface 1 according to FIG. 3, the level of the fluid 11 ending below the height of the opening 6. In this case, the belt 15 is connected to a bag 17 filled with a coupling fluid 18, which upon placing the belt 15 on the patient is in direct contact with the body section to be treated. On the other hand, this bag 17 dips into the precursor fluid section 11. The adjustment of the focus to the stone which is to be disintegrated is then performed in the manner described in the foregoing. An X-ray check is advantageously performed as soon as a stone has been disintegrated within the body of a patient. An X-ray apparatus 19 is installed at one extremity of the table surface 3 either in freestanding manner or fastened to the table 3, for this check. In the latter case, it is appropriate for the support 2 to be immobilisable in two locked positions on the table 3, of which the one position is determined by the setting of the shock wave generator, and the other position is determined by the setting of the X-ray apparatus 19. In the X-ray check position, the verification is performed by means of an image converter 20 or by means of film exposures.

We claim:

1. Apparatus for locating and disintegrating concretions within body cavities by means of shock waves, the apparatus comprising:
    a reclining surface for a patient comprising an operating table and a patient support positioned on the table, the operating table and the patient support having an opening formed therein for location of a part of the patient's body which is to be treated, the opening passing through both the operating table and the patient support;
    a shock wave generator comprising means for generating focussed shock waves;
    means for coupling shock waves from the shock wave generator through said opening to the part of the patient's body which is to be treated, the means for coupling comprising at least a flexibly constructed precursor fluid section coupled with the shock wave generator, the precursor fluid section comprising at least a flexible casing extending from the shock wave generator and a body of fluid contained in the flexible casing;
    means for establishing movement of the patient support between at least two positions, one selected for disintegrating the concretion within the body part, the other selected for x-ray exposure of the patient;
    means for sealing an upper portion of the flexible casing to the periphery of the opening in the table;
    a bag containing a coupling fluid; and
    a belt for securing the bag to the patient's body such that the bag projects through the opening in the table into contact with the fluid in the flexible casing and the bag and coupling fluid therein comprise means for coupling shock waves from the fluid in the flexible casing to the patient's body.

2. The apparatus of claim 1, the means for establishing movement comprising means for mounting the patient support on the table for movement between the at least two positions.

3. The apparatus of claim 2, further comprising means for generating an X-ray image by passing X-rays through the patient and the opening in the patient support when the patient support is disposed in one of the at least two positions.

4. The apparatus of claim 1, the means for establishing movement comprising means for mounting the patient support on the table for movement between a first position in which the opening in the patient support is disposed substantially above the shock wave generator and a second position in which the opening in the patient support is not disposed substantially above the shock wave generator.

5. The apparatus of claim 4, further comprising means for generating an X-ray image by passing X-rays through the patient and the opening in the patient support when the patient support is disposed in the second position.

6. The apparatus of claim 1, comprising means for coupling shock waves from the shock wave generator through an elastic diaphragm to the part of the patient's body which is to be treated.

7. The apparatus of claim 1, wherein the shock wave generator is mounted on a displacing unit.

8. The apparatus of claim 7, wherein the shock wave generator is mounted for pivotal movement into an inclined position with respect to the vertical.

9. Apparatus for locating and disintegrating concretions within body cavities by means of shock waves, the apparatus comprising:
    a reclining surface for a patient comprising an operating table and a patient support positioned on the table, the operating table and the patient support having an opening formed therein for location of a part of the patient's body which is to be treated, the opening passing through both the operating table and the patient support;

a shock wave generator comprising means for generating focussed shock waves;

means for coupling shock waves from the shock wave generator through said opening to the part of the patient's body which is to be treated, the means for coupling comprising at least a flexibly constructed precursor fluid section coupled with the shock wave generator, the precursor fluid section comprising at least a flexible casing extending from the shock wave generator and a body of fluid contained in the flexible casing;

means for establishing movement of the patient support between at least two positions, one selected for disintegrating the concretion within the body part, the other selected for x-ray exposure of the patient;

an upper end of the flexible casing being fastened to the table, the body of fluid in the flexible casing coupling the shock wave generator with the patient's body through the opening, the apparatus comprising an elastic seal disposed on an upper side of the patient support and being adapted to fit against the patient's body to seal against leakage of the body of fluid.

10. The apparatus of claim 9, the means for establishing movement comprising means for mounting the patient support on the table for movement between the at least two positions.

11. The apparatus of claim 10, further comprising means for generating an X-ray image by passing X-rays through the patient and the opening in the patient support when the patient support is disposed in one of the at least two positions.

12. The apparatus of claim 9, the means for establishing movement comprising means for mounting the patient support on the table for movement between a first position in which the opening in the patient support is disposed substantially above the shock wave generator and a second position in which the opening in the patient support is not disposed substantially above the shock wave generator.

13. The apparatus of claim 12, further comprising means for generating an X-ray image by passing X-rays through the patient and the opening in the patient support when the patient support is disposed in the second position.

* * * * *